(12) United States Patent
Humphreys et al.

(10) Patent No.: US 8,888,852 B2
(45) Date of Patent: Nov. 18, 2014

(54) SPINAL ATHROPLASTY DEVICE AND METHOD

(75) Inventors: Steven C. Humphreys, Chattanooga, TN (US); Scott D. Hodges, Ooltewah, TN (US)

(73) Assignee: HH Spinal LLC, Chattanooga, TN (US)

( * ) Notice: Subject to any disclaimer, the term of this patent is extended or adjusted under 35 U.S.C. 154(b) by 954 days.

(21) Appl. No.: 12/484,725

(22) Filed: Jun. 15, 2009

(65) Prior Publication Data

US 2009/0254183 A1    Oct. 8, 2009

Related U.S. Application Data

(63) Continuation of application No. 11/031,602, filed on Jan. 7, 2005, now Pat. No. 7,550,010.

(60) Provisional application No. 60/534,960, filed on Jan. 9, 2004.

(51) Int. Cl.
*A61F 2/44* (2006.01)
*A61F 2/30* (2006.01)
*A61F 2/28* (2006.01)

(52) U.S. Cl.
CPC ..... *A61F 2/4425* (2013.01); *A61F 2002/30578* (2013.01); *A61F 2002/30884* (2013.01); *A61F 2310/00796* (2013.01); *A61F 2002/30331* (2013.01); *A61F 2/4405* (2013.01); *A61F 2002/30616* (2013.01); *A61F 2220/0033* (2013.01); *A61F 2002/30665* (2013.01); *A61F 2002/30507* (2013.01); *A61F 2002/30654* (2013.01); *A61F 2002/30662* (2013.01); *A61F 2002/30604* (2013.01); *A61F 2002/30649* (2013.01); *A61F 2310/00203* (2013.01); *A61F 2002/2817* (2013.01); *A61F 2002/3082* (2013.01); *A61F 2002/30925* (2013.01); *A61F 2310/00167* (2013.01); *A61F 2310/00161* (2013.01); *A61F 2220/0025* (2013.01); *A61F 2310/00239* (2013.01); *A61F 2002/30841* (2013.01)
USPC ..................................................... 623/17.15

(58) Field of Classification Search
CPC ..... A61F 2/4611; A61F 2/4455; A61F 2/442; A61F 2/44; A61F 2/28; A61F 2/30
USPC ........................................... 623/17.11–17.16
See application file for complete search history.

(56) References Cited

U.S. PATENT DOCUMENTS

| | | |
|---|---|---|
| 4,349,921 A | 9/1982 | Kuntz |
| 4,697,582 A | 10/1987 | Williams |

(Continued)

FOREIGN PATENT DOCUMENTS

| | | |
|---|---|---|
| DE | 101 35771 A1 | 2/2003 |
| DE | 20 2004 015198 | 11/2004 |

(Continued)

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000648, Jun. 6, 2005, 6 pages.

(Continued)

*Primary Examiner* — David Isabella
*Assistant Examiner* — Ann Schillinger
(74) *Attorney, Agent, or Firm* — Bachman & LaPointe, P.C.

(57) ABSTRACT

An artificial spinal joint and methods for replacing at least a portion of a natural intervertebral disc are provided. In some embodiments, at least portions of facet joints are replaced along with the intervertebral disc.

19 Claims, 5 Drawing Sheets

(56) References Cited

U.S. PATENT DOCUMENTS

| | | |
|---|---|---|
| 4,702,930 A | 10/1987 | Heide et al. |
| 4,759,769 A | 7/1988 | Hedman et al. |
| 4,932,975 A | 6/1990 | Main et al. |
| 5,092,866 A | 3/1992 | Breard et al. |
| 5,258,031 A * | 11/1993 | Salib et al. ............... 623/17.15 |
| 5,282,863 A | 2/1994 | Burton |
| 5,387,213 A | 2/1995 | Breard et al. |
| 5,401,269 A | 3/1995 | Buttner-Janz et al. |
| 5,415,661 A | 5/1995 | Holmes |
| 5,443,515 A | 8/1995 | Cohen et al. |
| 5,458,864 A | 10/1995 | Tsugeno et al. |
| 5,507,816 A | 4/1996 | Bullivant |
| 5,556,431 A | 9/1996 | Buttner-Janz |
| 5,562,660 A | 10/1996 | Grob |
| 5,562,737 A | 10/1996 | Graf |
| 5,562,738 A | 10/1996 | Boyd et al. |
| 5,672,175 A | 9/1997 | Martin |
| 5,674,296 A | 10/1997 | Bryan et al. |
| 5,676,701 A | 10/1997 | Yuan et al. |
| 5,702,450 A | 12/1997 | Bisserie |
| 5,895,428 A | 4/1999 | Berry |
| 5,899,941 A | 5/1999 | Nishijima et al. |
| RE36,221 E | 6/1999 | Breard et al. |
| 5,928,284 A | 7/1999 | Mehdizadeh |
| 5,961,516 A | 10/1999 | Graf |
| 6,019,792 A | 2/2000 | Cauthen |
| 6,036,088 A | 3/2000 | Itoh et al. |
| 6,039,763 A | 3/2000 | Shelokov |
| 6,042,582 A | 3/2000 | Ray |
| RE36,758 E | 6/2000 | Fitz |
| 6,106,557 A | 8/2000 | Robioneck et al. |
| 6,113,637 A | 9/2000 | Gill et al. |
| 6,132,464 A | 10/2000 | Martin |
| 6,146,421 A | 11/2000 | Gordon et al. |
| 6,156,067 A | 12/2000 | Bryan et al. |
| 6,159,211 A | 12/2000 | Boriani et al. |
| 6,159,214 A | 12/2000 | Michelson |
| 6,159,244 A | 12/2000 | Suddaby |
| 6,174,311 B1 | 1/2001 | Branch et al. |
| 6,179,874 B1 | 1/2001 | Cauthen |
| 6,179,875 B1 | 1/2001 | Strempel |
| 6,190,414 B1 | 2/2001 | Young et al. |
| 6,193,757 B1 | 2/2001 | Foley et al. |
| 6,200,322 B1 | 3/2001 | Branch et al. |
| 6,224,599 B1 | 5/2001 | Baynham et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,059 B1 | 5/2001 | Benezech et al. |
| 6,238,396 B1 | 5/2001 | Lombardo |
| 6,251,112 B1 | 6/2001 | Jackson |
| 6,277,122 B1 | 8/2001 | McGahan et al. |
| 6,325,827 B1 | 12/2001 | Lin |
| 6,368,350 B1 | 4/2002 | Erickson et al. |
| 6,387,130 B1 | 5/2002 | Stone et al. |
| 6,402,750 B1 | 6/2002 | Atkinson et al. |
| 6,409,766 B1 | 6/2002 | Brett |
| 6,419,703 B1 | 7/2002 | Fallin et al. |
| 6,419,705 B1 | 7/2002 | Erickson |
| 6,432,140 B1 | 8/2002 | Lin |
| 6,440,139 B2 | 8/2002 | Michelson |
| 6,440,168 B1 | 8/2002 | Cauthen |
| 6,454,807 B1 | 9/2002 | Jackson |
| 6,471,724 B2 | 10/2002 | Zdeblick et al. |
| 6,514,260 B1 | 2/2003 | Zdeblick et al. |
| 6,517,580 B1 | 2/2003 | Ramadan et al. |
| 6,524,312 B2 | 2/2003 | Landry et al. |
| 6,527,804 B1 | 3/2003 | Gauchet et al. |
| 6,540,747 B1 | 4/2003 | Marino |
| 6,540,785 B1 | 4/2003 | Gill et al. |
| 6,562,074 B2 | 5/2003 | Gerbec et al. |
| 6,565,571 B1 | 5/2003 | Jackowski et al. |
| 6,565,574 B2 | 5/2003 | Michelson |
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,468 B1 | 6/2003 | Gauchet |
| 6,589,247 B2 | 7/2003 | McGahan et al. |
| 6,599,291 B1 | 7/2003 | Foley et al. |
| 6,610,065 B1 | 8/2003 | Branch et al. |
| 6,610,091 B1 | 8/2003 | Reiley |
| 6,610,093 B1 | 8/2003 | Pisharodi |
| 6,641,582 B1 | 11/2003 | Hanson et al. |
| 6,641,614 B1 | 11/2003 | Wagner et al. |
| 6,648,895 B2 | 11/2003 | Burkus et al. |
| 6,669,729 B2 | 12/2003 | Chin |
| 6,679,915 B1 | 1/2004 | Cauthen |
| 6,685,742 B1 | 2/2004 | Jackson |
| 6,692,495 B1 | 2/2004 | Zacouto |
| 6,699,247 B2 | 3/2004 | Zucherman et al. |
| 6,709,458 B2 | 3/2004 | Michelson |
| 6,733,532 B1 | 5/2004 | Gauchet et al. |
| 6,743,255 B2 | 6/2004 | Ferree |
| 6,749,635 B1 | 6/2004 | Bryan |
| 6,805,714 B2 | 10/2004 | Sutcliffe |
| 6,811,567 B2 | 11/2004 | Reiley |
| 6,908,484 B2 | 6/2005 | Zubok et al. |
| 6,949,123 B2 | 9/2005 | Reiley |
| 6,984,245 B2 | 1/2006 | McGahan et al. |
| 6,986,772 B2 | 1/2006 | Michelson |
| 6,994,727 B2 | 2/2006 | Khandkar et al. |
| 7,025,787 B2 | 4/2006 | Bryan et al. |
| 7,044,971 B2 | 5/2006 | Suddaby |
| 7,052,515 B2 | 5/2006 | Simonson |
| 7,070,598 B2 | 7/2006 | Lim et al. |
| 7,074,240 B2 | 7/2006 | Pisharodi |
| 7,083,649 B2 | 8/2006 | Zucherman et al. |
| 7,083,650 B2 | 8/2006 | Moskowitz et al. |
| 7,090,698 B2 | 8/2006 | Goble et al. |
| 7,137,985 B2 | 11/2006 | Jahng |
| 7,147,665 B1 | 12/2006 | Bryan et al. |
| 7,282,065 B2 | 10/2007 | Kirschman |
| 7,291,150 B2 | 11/2007 | Graf |
| 7,311,732 B2 | 12/2007 | Link et al. |
| 7,338,525 B2 | 3/2008 | Ferree |
| 7,338,527 B2 | 3/2008 | Blatt et al. |
| 7,550,010 B2 | 6/2009 | Humphreys et al. |
| 2001/0005796 A1 | 6/2001 | Zdeblick et al. |
| 2001/0010021 A1 | 7/2001 | Boyd et al. |
| 2001/0016773 A1 | 8/2001 | Serhan et al. |
| 2001/0016774 A1 | 8/2001 | Bresina et al. |
| 2001/0032020 A1 | 10/2001 | Besselink |
| 2001/0034553 A1 | 10/2001 | Michelson |
| 2001/0047207 A1 | 11/2001 | Michelson |
| 2001/0049560 A1 | 12/2001 | Paul et al. |
| 2002/0045943 A1 | 4/2002 | Uk |
| 2002/0049394 A1 | 4/2002 | Roy et al. |
| 2002/0049497 A1 | 4/2002 | Mason |
| 2002/0052656 A1 | 5/2002 | Michelson |
| 2002/0068976 A1 | 6/2002 | Jackson |
| 2002/0068977 A1 | 6/2002 | Jackson |
| 2002/0077702 A1 | 6/2002 | Castro |
| 2002/0095154 A1 | 7/2002 | Atkinson et al. |
| 2002/0095155 A1 | 7/2002 | Michelson |
| 2002/0107572 A1 | 8/2002 | Foley et al. |
| 2002/0116065 A1 | 8/2002 | Jackson |
| 2002/0123806 A1 | 9/2002 | Reiley |
| 2002/0128712 A1 | 9/2002 | Michelson |
| 2002/0128713 A1 | 9/2002 | Ferree |
| 2002/0133155 A1 | 9/2002 | Ferree |
| 2002/0138143 A1 | 9/2002 | Grooms et al. |
| 2002/0138146 A1 | 9/2002 | Jackson |
| 2002/0143399 A1 | 10/2002 | Sutcliffe |
| 2002/0151895 A1 | 10/2002 | Soboleski et al. |
| 2002/0151976 A1 | 10/2002 | Foley et al. |
| 2002/0156528 A1 | 10/2002 | Gau |
| 2002/0161366 A1 | 10/2002 | Robie et al. |
| 2002/0169508 A1 | 11/2002 | Songer et al. |
| 2002/0183756 A1 | 12/2002 | Michelson |
| 2003/0004572 A1 | 1/2003 | Goble et al. |
| 2003/0004575 A1 | 1/2003 | Erickson |
| 2003/0009226 A1 | 1/2003 | Graf |
| 2003/0028250 A1 | 2/2003 | Reiley et al. |

(56) References Cited

U.S. PATENT DOCUMENTS

| | | |
|---|---|---|
| 2003/0040797 A1 | 2/2003 | Fallin et al. |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Ferree |
| 2003/0208273 A1 | 11/2003 | Eisermann et al. |
| 2003/0220643 A1 * | 11/2003 | Ferree .................... 606/61 |
| 2003/0233146 A1 | 12/2003 | Grinberg et al. |
| 2004/0002712 A1 | 1/2004 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1 | 2/2004 | Pisharodi |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |
| 2004/0073311 A1 | 4/2004 | Ferree |
| 2004/0097931 A1 | 5/2004 | Mitchell |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186570 A1 | 9/2004 | Rapp |
| 2004/0186577 A1 | 9/2004 | Ferree |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0243240 A1 | 12/2004 | Beaurain et al. |
| 2004/0243241 A1 | 12/2004 | Istephanous et al. |
| 2004/0249461 A1 | 12/2004 | Ferree |
| 2004/0254643 A1 | 12/2004 | Jackson |
| 2005/0027359 A1 | 2/2005 | Mashburn |
| 2005/0043800 A1 | 2/2005 | Paul et al. |
| 2005/0043802 A1 | 2/2005 | Eisermann et al. |
| 2005/0071008 A1 | 3/2005 | Kirschman |
| 2005/0075644 A1 | 4/2005 | DiPoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |
| 2005/0119747 A1 | 6/2005 | Fabris Monterumici et al. |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Humphreys et al. |
| 2005/0154462 A1 | 7/2005 | Zucherman et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1 | 8/2005 | Peterman et al. |
| 2005/0171610 A1 | 8/2005 | Humphreys et al. |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1 | 9/2005 | Taylor |
| 2005/0234551 A1 | 10/2005 | Fallin et al. |
| 2005/0234555 A1 | 10/2005 | Sutton et al. |
| 2005/0240270 A1 | 10/2005 | Zubok et al. |
| 2005/0256578 A1 | 11/2005 | Blatt et al. |
| 2005/0261773 A1 | 11/2005 | Ferree |
| 2005/0261774 A1 | 11/2005 | Trieu |
| 2005/0277930 A1 | 12/2005 | Parsons |
| 2005/0277938 A1 | 12/2005 | Parsons |
| 2005/0283237 A1 | 12/2005 | Zucherman et al. |
| 2006/0004448 A1 | 1/2006 | Casey |
| 2006/0009849 A1 | 1/2006 | Reiley |
| 2006/0036325 A1 | 2/2006 | Paul et al. |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |
| 2006/0247650 A1 | 11/2006 | Yerby et al. |
| 2007/0055378 A1 | 3/2007 | Ankney et al. |
| 2007/0270972 A1 | 11/2007 | Gordon et al. |
| 2008/0015693 A1 | 1/2008 | LeCouedic |
| 2008/0045968 A1 | 2/2008 | Yu et al. |
| 2008/0300685 A1 | 12/2008 | Carls et al. |
| 2009/0259255 A1 | 10/2009 | Humphreys et al. |

FOREIGN PATENT DOCUMENTS

| | | |
|---|---|---|
| DE | 202004015198 | 11/2004 |
| EP | 0 677 277 A2 | 10/1995 |
| EP | 1 281 361 A1 | 2/2003 |
| EP | 1685811 | 8/2006 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |
| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |
| WO | WO 2004/098465 | 11/2004 |
| WO | WO2005025431 | 3/2005 |
| WO | WO2005067824 | 7/2005 |
| WO | WO2005070350 | 8/2005 |
| WO | WO2005070353 | 8/2005 |
| WO | WO 2005/112835 | 12/2005 |
| WO | WO2005112835 | 12/2005 |
| WO | WO2005117725 | 12/2005 |

(56) References Cited

FOREIGN PATENT DOCUMENTS

WO   WO2007087477   8/2007
WO   WO2007124467   11/2007

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.

Patent Cooperation Treaty—European Patent Office, "Invitation to Pay Additional Fees/Communication Relating to the Results of the Partial International Search," International Application No. PCT/US2005/000586, Jun. 8, 2005, 5 pages.

Patent Cooperation Treaty—European Patent Office, "Notification of Transmittal of the International Search Report and the Written Opinion of the International Searching Authority, or the Declaration," International Application No. PCT/US2005/000585, Jun. 8, 2005, 6 pages.

Patent Cooperation Treaty—European Patent Office, "Notification of Transmittal of the International Search Report and the Written Opinion of the International Searching Authority, or the Declaration," International Application No. PCT/US2005/000704, Aug. 23, 2005, 7 pages.

Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.

Yu, et al., U.S. Appl. No. 11/342,961, filed Jan. 30, 2006, 39 pages.
Braddock, et al., U.S. Appl. No. 11/343,159, filed Jan. 30, 2006, 40 pages.
Yu, et al., U.S. Appl. No. 11/393,488, filed Mar. 30, 2006, 26 pages.
Yu, et al., U.S. Appl. No. 11/494,311, filed Jul. 27, 2006, 54 pages.

Patent Cooperation Treaty—European Patent Office, "Notification of Transmittal of the International Search Report and the Written Opinion of the International Searching Authority, or the Declaration," International Application No. PCT/US2007/060491, Apr. 25, 2007, 12 pages.

Patent Cooperation Treaty—European Patent Office, "Notification of Transmittal of the International Search Report and the Written Opinion of the International Searching Authority, or the Declaration," International Application No. PCT/US2007/060549, Feb. 10, 2007, 20 pages.

Patent Cooperation Treaty—European Patent Office, "Notification of Transmittal of the International Search Report and the Written Opinion of the International Searching Authority, or the Declaration," International Application No. PCT/US2007/074385, Dec. 19, 2007, 13 pages.

Patent Cooperation Treaty—European Patent Office, "Notification of Transmittal of the International Search Report and the Written Opinion of the International Searching Authority, or the Declaration," International Application No. PCT/US2007/065504, Mar. 3, 2009, 12 pages.

Patent Cooperation Treaty—European Patent Office, "Notification of Transmittal of the International Search Report and the Written Opinion of the International Searching Authority, or the Declaration," International Application No. PCT/US2005/000586, Dec. 16, 2005, 8 pages.

* cited by examiner

SPINAL ATHROPLASTY DEVICE AND METHOD

CROSS REFERENCE

This application is a continuation of U.S. patent application Ser. No. 11/031,602 filed Jan. 7, 2005, entitled "Spinal Arthroplasty Device and Method," which claims priority from U.S. Provisional Patent Application Ser. No. 60/534,960 filed on Jan. 9, 2004, entitled "Posterior Lumbar Arthroplasty." These applications are incorporated by reference herein. The following applications also claim priority to the above referenced provisional application and are related to the present application. They are incorporated by reference herein.

- U.S. Utility patent application Ser. No. 11/031,603, filed on Jan. 7, 2005 and entitled "Dual Articulating Spinal Device and Method;"
- U.S. Utility patent application Ser. No. 11/031,780, filed on Jan. 7, 2005 and entitled "Split Spinal Device and Method;"
- U.S. Utility patent application Ser. No. 11/031,904, filed on Jan. 7, 2005 and entitled "Interconnected Spinal Device and Method;"
- U.S. Utility patent application Ser. No. 11/031,783 filed on Jan. 7, 2005 and entitled "Mobile Bearing Spinal Device and Method;"
- U.S. Utility patent application Ser. No. 11/031,700, filed on Jan. 7, 2005 and entitled "Support Structure Device and Method;"
- U.S. Utility patent application Ser. No. 11/031,781, filed on Jan. 7, 2005 and entitled "Centrally Articulating Spinal Device and Method;" and
- U.S. Utility patent application Ser. No. 11/031,903, filed on Jan. 7, 2005 and entitled "Posterior Spinal Device and Method."

TECHNICAL FIELD

Embodiments of the invention relate generally to devices and methods for accomplishing spinal surgery, and more particularly in some embodiments, to spinal arthroplasty devices capable of being placed posteriorly into the vertebral disc space. Various implementations of the invention are envisioned, including use in total spine arthroplasty replacing, via a posterior approach, both the disc and facet functions of a natural spinal joint.

BACKGROUND

Figure 1:
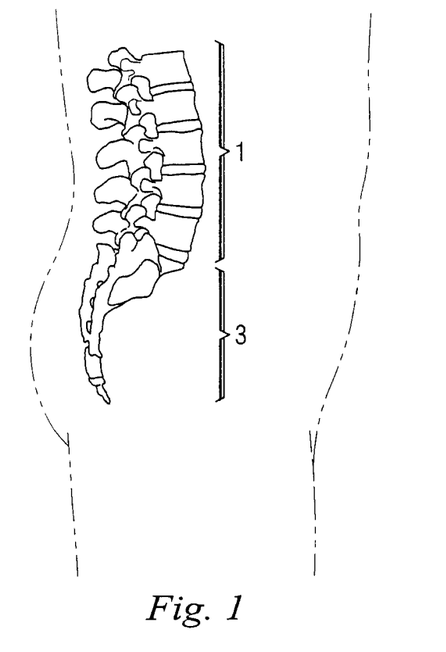
FIG. 1 is a side elevation schematic view of the lumbar spinal and the sacrum regions of a healthy, human spinal column.

As is known the art, in the human anatomy, the spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made up of individual bones called vertebrae and the vertebrae are separated by intervertebral discs which are situated therebetween.

Figure 2:
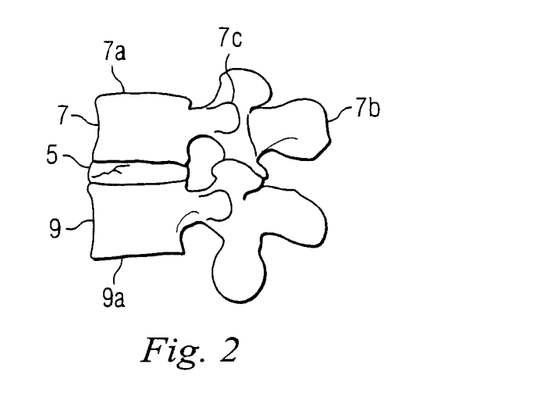
FIG. 2 is a detailed perspective view showing a portion of the right side of the lumbar vertebrae shown in FIG. 1 with a healthy disc disposed between two vertebrae.
Figure 3:
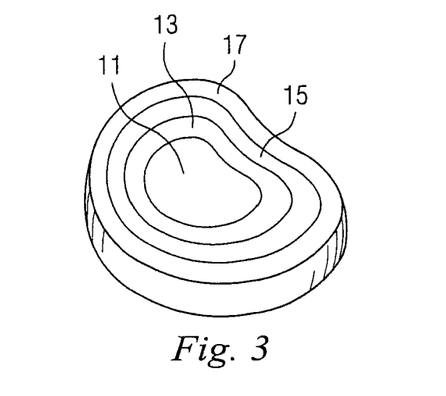
FIG. 3 is a top perspective view of the intervertebral disc shown in FIG. 2 illustrating the major portions of the disc.
Figure 7A:
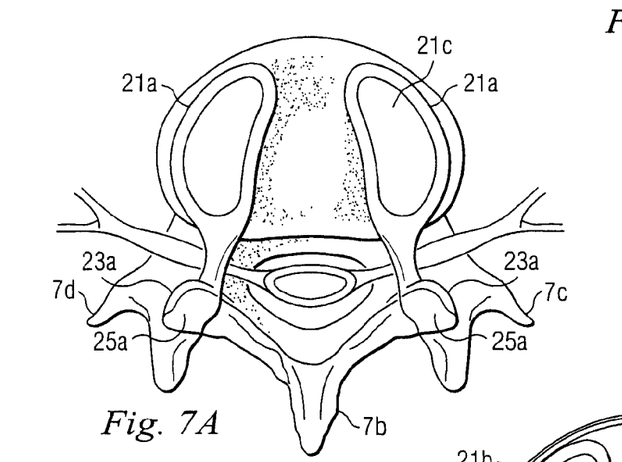
FIG. 7A is a transverse, bottom-up-view of a portion of a lumbar spine showing the superior portion of the artificial intervertebral joint illustrated in FIG. 4.

FIG. 2 illustrates a portion of the right side of a lumbar spinal region with a healthy intervertebral disc 5 disposed between two adjacent vertebrae 7, 9. In any given joint, the top vertebra may be referred to as the superior vertebra and the bottom one as the inferior vertebra. Each vertebra comprises a generally cylindrical body 7a, 9a, which is the primary area of weight bearing, and three bony processes, e.g., 7b, 7c, 7d (two of which are visible in FIG. 2). As shown in FIG. 7A, in which all of the processes are visible, processes 7b, 7c, 7d extend outwardly from vertebrae body 7 at circumferentially spaced locations. The processes, among other functions, provide areas for muscle and ligament attachment. Neighboring vertebrae may move relative to each other via facet components 7e (FIG. 2), which extend from the cylindrical body of the vertebrae and are adapted to slide one over the other during bending to guide movement of the spine. There are two facet joints, each defined by upper and lower facet components, associated with adjacent vertebra. A healthy intervertebral disc is shown in FIG. 3. As shown in FIG. 3, an intervertebral disc has 4 regions: a nucleus pulposus 11, a transition zone 13, an inner annulus fibrosis region 15 and an outer annulus fibrosis 17. Generally, the inner annulus fibrosis region 15 and the outer annulus fibrosis region 17 are made up of layers of a fibrous gristly material firmly attached to the vertebral bodies above and below it. The nucleus pulposus 11 is typically more hydrated in nature.

These intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorally and/or posteriorally. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but for some patients maintaining motion may be advantageous. It is also known to surgically replace a degenerative disc or facet joint with an artificial disc or an artificial facet joint, respectively. However, none of the known devices or methods provide the advantages of the embodiments of the present disclosure.

Accordingly, the foregoing shows there is a need for an improved spinal arthroplasty that avoids the drawbacks and disadvantages of the known implants and surgical techniques.

SUMMARY

A first embodiment of this disclosure provides an artificial spinal joint for creating at least a portion of a coupling between a superior vertebra and an inferior vertebra. The artificial spinal joint may include an anterior joint replacement component and a bridge coupled to the anterior joint replacement that extends posteriorly from the anterior joint replacement. Additionally, a posterior joint replacement component may be coupled to the bridge as part of the artificial spinal joint.

In another embodiment, the artificial spinal joint includes an anterior joint replacement component with a left upper member, a left lower member that articulates with the left upper member, a right upper member, and a right lower member that articulates with the right upper member. In this embodiment, the left lower member and the right lower member are each configured to connect to the other.

In still another embodiment, this disclosure describes a method of implanting an artificial spinal joint. The method includes making an incision in a patient's back, removing at least a portion of spinal disc material from a spinal disc, the removing comprising accessing the disc material through the incision, and inserting an implant through the incision. In this embodiment, an implant that replaces at least a portion of a disc and a facet joint is inserted.

The embodiments disclosed may be useful for degenerative changes of the lumbar spine, post-traumatic, discogenic, facet pain or spondylolisthesis, and/or to maintain motion in multiple levels of the lumbar spine.

Additional and alternative features, advantages, uses and embodiments are set forth in or will be apparent from the following description, drawings, and claims.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 4:
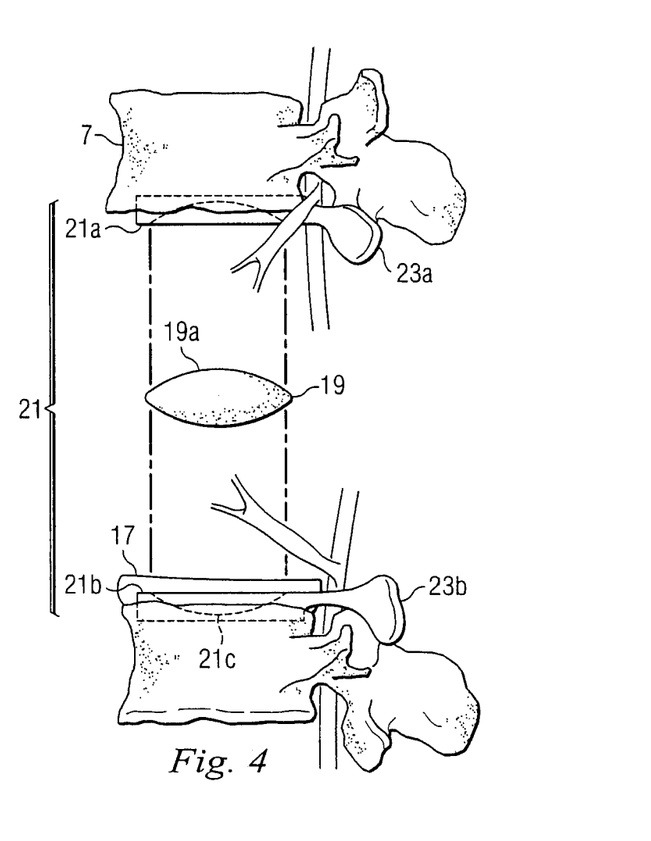
FIG. 4 is a side exploded elevation view of a portion of a lumbar spine showing a first embodiment of an artificial intervertebral joint constructed according to the principles of the disclosure.
Figure 5:
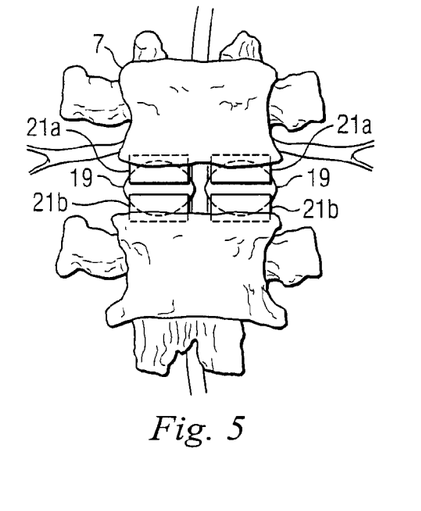
FIG. 5 is an anterior elevation view of a portion of a lumbar spine showing the superior, disc and inferior portions of the left and right halves of an assembled artificial intervertebral joint constructed according to the first embodiment of the disclosure.

FIGS. 4-7 illustrate a first exemplary embodiment of an artificial intervertebral joint. As illustrated in FIGS. 4 and 5, each joint is composed of two arthroplasty halves, each of which has a spacer or disc 19 and a retaining portion 21. The retaining portion 21 includes a first retaining portion 21a and a second retaining portion 21b. In the example illustrated in FIG. 4, the first retaining portion 21a is superior to (above) the second retaining portion 21b and the disc 19 is situated therebetween. Although the artificial intervertebral joint according to this exemplary embodiment has two halves for each of the first retaining portion and the second retaining portion, it should be understood that alternative embodiments may be implemented such that the artificial intervertebral joint has a single first retaining member, a single second retaining member and a single spacer. It should also be understood that alternative embodiments may also be carried out with arthroplasties having a first retaining portion, a second retaining portion, and/or a disc which each consist of unequal sized halves or more than two components.

Further, as illustrated in FIG. 4, the first retaining portion 21a and the second retaining portion 21b are situated between two adjacent vertebrae. Mote particularly, the first retaining portion may be situated along an inferior surface of the upper of the two adjacent vertebrae and the second retaining portion may be situated above a superior surface of the lower of the two adjacent vertebrae. However, it should be understood by one of ordinary skill in the art that the first retaining portion and second retaining portion are not limited to such an arrangement, and may be oriented in different positions and/or shaped differently than what is illustrated herein.

The surfaces of the retaining portions 21a, 21b of the arthroplasty that contact the remaining end plates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

As discussed in more detail below, a significant portion of the outer annulus region 17 (see, e.g., FIGS. 4, 7B), in some embodiments about 300 degrees, may be retained on the inferior portion of the end plate, which acts as a stop retaining the lower retaining portions in place until bone ingrowth occurs to firmly attach the retaining portions to their respective vertebrae (FIG. 4 only shows a portion of the outer annulus 17 that is retained). In contrast, in conventional anterior arthroplasty about 270 degrees of the outer annulus region 17 typically is removed. In addition, pedicle screws may also be used for immediate fixation as described in more detail in connection with other embodiments discussed below.

In the various embodiments of this disclosure, the first retaining portion 21a and the second retaining portion 21b are structured so as to retain the disc 19 therebetween. For example, in the case of a disc 19 with two convex surfaces 19a, each of the first retaining portion 21a and the second retaining portion 21b may have a concave surface 21c which defines a space within which the disc 19 may be retained. For example, in the exemplary embodiment shown in FIG. 4, the upper convex surface 19a of the disc 19 fits within the concavity defined by the concave surface 21c of the first retaining portion 21a and the lower convex surface 19b of the disc 19 fits within the concavity defined by the concave surface 21c of the second retaining portion 21b.

Figure 6:
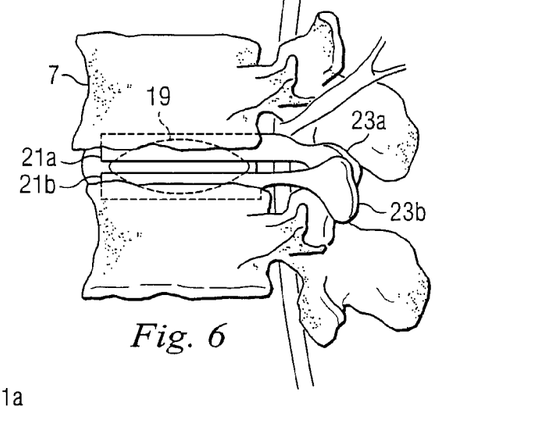
FIG. 6 is a side elevation view of the right half of the artificial intervertebral joint shown in FIG. 5.

FIG. 5 illustrates an anterior view of an exemplary assembled artificial intervertebral joint with both arthroplasty halves in place, and FIG. 6 shows a side view of the assembled artificial intervertebral joint shown in FIG. 5. As illustrated in FIGS. 5 and 6, the disc 19 is retained between the first retaining portion 21a and the second retaining portion 21b. It should be understood that although the disc 19 may be held between the first retaining portion 21a and the second retaining portion 21b, the disc 19 is free to slidably move within the space defined by the corresponding surfaces 21a of the first retaining portion 21a and the second retaining portion 21b. In this manner, limited movement between the adjacent vertebrae is provided.

In the exemplary embodiment illustrated in FIGS. 4, 5 and 6, the disc 19 is a separate component which is inserted between the first retaining portion 21a and the second retaining portion 21b. However, as discussed below, it should be understood that the spacer or disc 19 may be integrally formed with or integrated into in one or both of the first retaining portion 21a and the second retaining portion 21b.

Figure 7B:
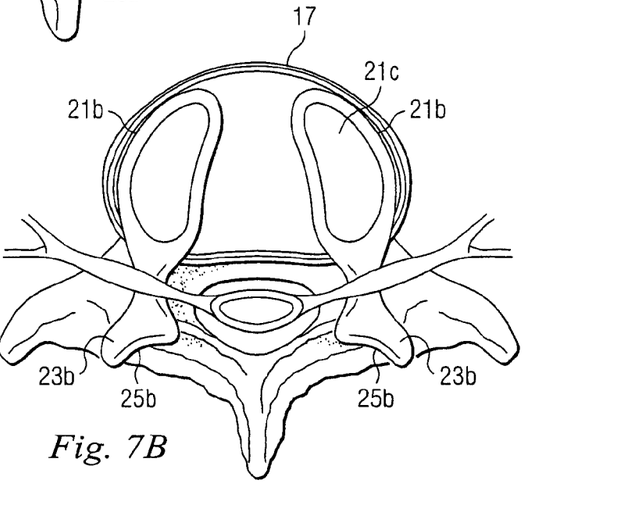
FIG. 7B is a transverse, top-down-view of a portion of a lumbar spine showing the inferior portion of the artificial intervertebral joint illustrated in FIG. 4.
Figures 8, 9, 10, 11:
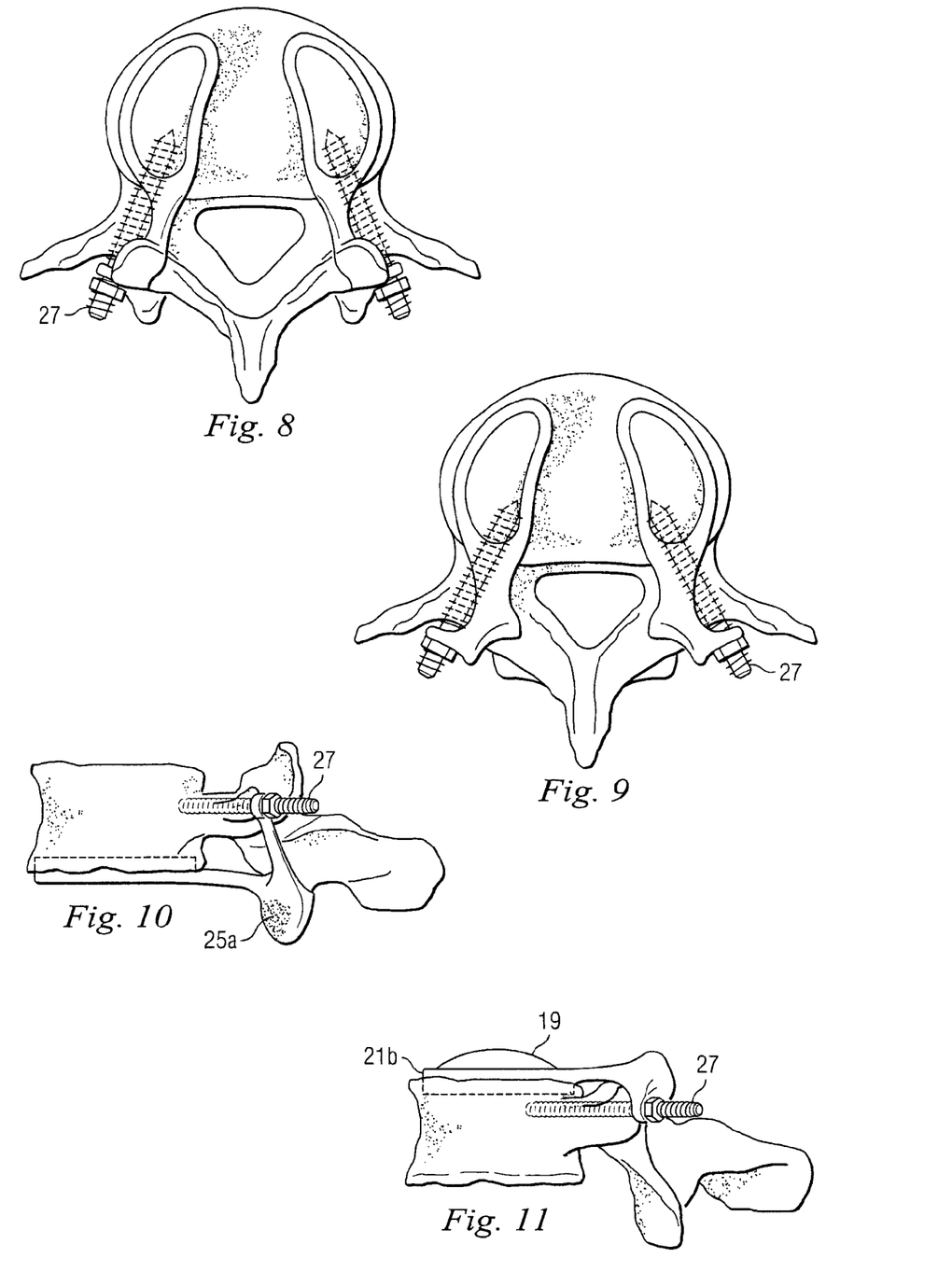
FIG. 8 is a transverse, bottom-up-view of a portion of a lumbar spine showing a second embodiment of a superior portion of an artificial intervertebral joint in which pedicle screws are used to assist in implantation.
FIG. 9 is a transverse, top-down-view of a portion of a lumbar spine showing a second embodiment of an inferior portion of an artificial intervertebral joint in which pedicle screws are used to assist in implantation.
FIG. 10 is a lateral view of a portion of a lumbar spine showing the superior portion of the artificial intervertebral joint shown in FIG. 8 with one of the pedicle screws being visible.
FIG. 11 is a lateral view of a portion of a lumbar spine showing the inferior and integrated disc portions of an artificial integral intervertebral joint shown in FIG. 9 with one of the pedicle screws being visible.
Figure 12:
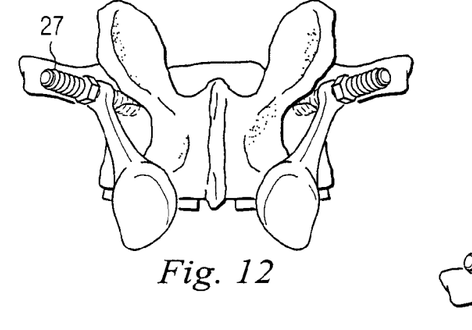
FIG. 12 is a posterior view of a portion of a lumbar spine showing the superior portion of the artificial intervertebral joint shown in FIG. 8 with two pedicle screws being visible.
Figure 13:
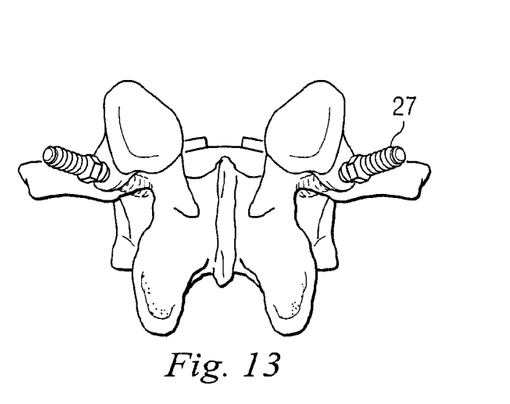
FIG. 13 is a posterior view of a portion of a lumbar spine showing the inferior portion of the artificial intervertebral joint shown in FIG. 9 with two pedicle screws being visible.
Figure 14:
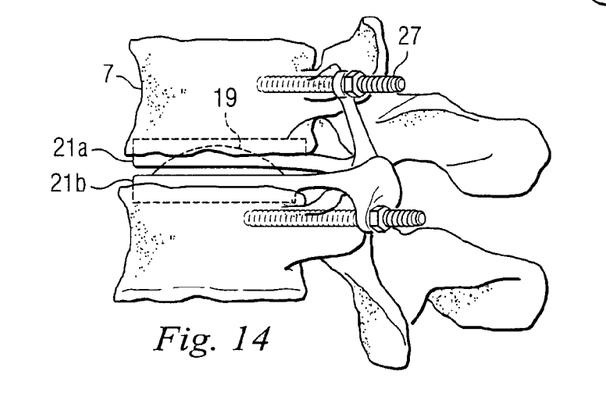
FIG. 14 is a side elevation view of a portion of a lumbar spine showing the second embodiment with pedicle screws in an assembled position.

In the exemplary embodiment of the disclosure, as illustrated best in FIGS. 4, 6, 7A and 7B, each of the retaining portions of the artificial intervertebral joint includes a first artificial facet component 23a and a second artificial facet component 23b. As shown in FIGS. 7A and 7B, the first artificial facet component 23a has a face 25a and the corresponding second artificial facet component 23b has a face 25b configured such that the face 25a matingly fits with the face 25b to stabilize adjacent vertebrae while preserving and guiding the mobility of each vertebrae with respect to the other vertebrae. Each set of the upper and lower retaining portions 21a, 21b may have a pair of facet components 23a, 23b, which together define a facet joint. For a total joint replacement with facets according to this embodiment, the left and right arthroplasties would define two adjacent facet joints when viewed from the posterior.

Regardless of whether artificial facet joints are provided, the respective upper and lower retaining portions associated with the left and right halves of the arthroplasty may be completely independent from the other. That is, as shown in FIG. 7A, for example, the first retaining portions 21a associated with each half are not in direct contact with each other. The same is true with respect to the second retaining portions 21b shown in FIG. 7B. However, it should be understood by one of ordinary skill in the art that, even in the embodiment of the disclosure which includes artificial facet joints, at least a portion of the first retaining portions 21a of each half and/or at least a portion of the second retaining portions 21b of each half may directly contact and/or be connected to each other as described in more detail in connection with the discussion of FIGS. 17-18.

Further, in the various embodiments of the disclosure, the disc 19, the first retaining portion 21a and the second retaining portion 21b may be made of any appropriate material which will facilitate a connection that transmits compressive and tensile forces while providing for the aforementioned slidable motion in a generally transverse direction between each of the adjacent surfaces. For example, in the first embodiment, the first retaining portion 21a and the second retaining portion 21b may be typically made from any metal or metal alloy suitable for surgical implants such as stainless steel, titanium, and cobalt chromium, or composite materials such as carbon fiber, or a plastic material such as polyetheretherketone (PEEK) or any other suitable materials. The disc may be made from plastic such as high molecular weight polyethylene or PEEK, or from ceramics, metal, and natural or synthetic fibers such as, but not limited to, carbon fiber, rubber, or other suitable materials. Generally, to help maintain the sliding characteristic of the surfaces, the surfaces may be polished and/or coated to provide smooth surfaces. For example, if the surfaces are made of metal, the metal surfaces may be polished metal.

FIGS. 8-14 illustrate a second embodiment of an artificial intervertebral joint. Only features that differ from the first embodiment are discussed in detail herein. In the second exemplary embodiment, securing components, such as, for example, pedicle screws 27 are provided to provide a more secure and immediate connection between each of the first retaining portion 21a and/or the second retaining portion 21b to the corresponding vertebra. In addition, this embodiment illustrates a disc 19 which is integrated with one of the retaining portions, here lower retaining portion 21b. Disc 19 may be integrally formed from the same material as its retaining portion, but also may be separately formed from similar or dissimilar materials and permanently connected thereto to form an integral unit. In this embodiment, the disc 19 and the retaining portions may be all formed from metal.

Figure 15:
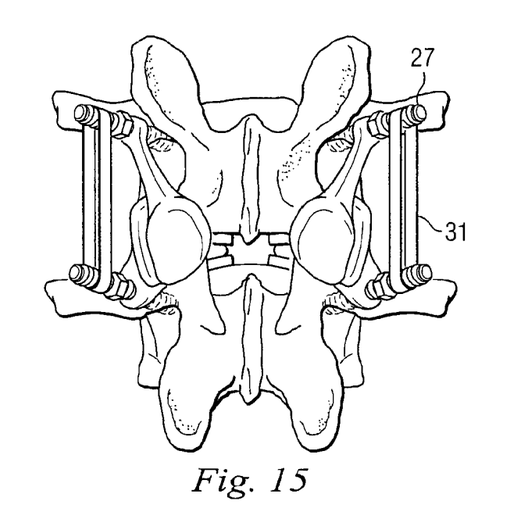
FIG. 15 is a posterior view of a portion of a lumbar spine showing a third embodiment of the inferior, disc and superior portions of an artificial intervertebral joint in which tension bands are used.
Figure 16:
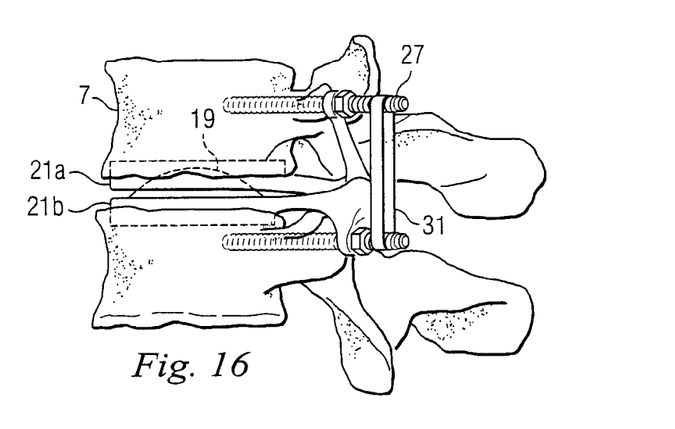
FIG. 16 is a side elevation view of a portion of a lumbar spine showing the third embodiment in which tension bands are used in an assembled position.

FIGS. 15 and 16 illustrate a third embodiment of an artificial intervertebral joint. In the third exemplary embodiment, additional securing components, such as, for example, tension bands 31 are provided to supplement or replace the function of posterior ligaments that limit the mobility between adjacent vertebrae by securing the first retaining portion 21a to the second retaining portion 21b. As shown in FIGS. 15-16, posterior tension bands 31 may be provided by wrapping them around the corresponding pedicle screws 27 or other convenient attachment points.

Figure 17:
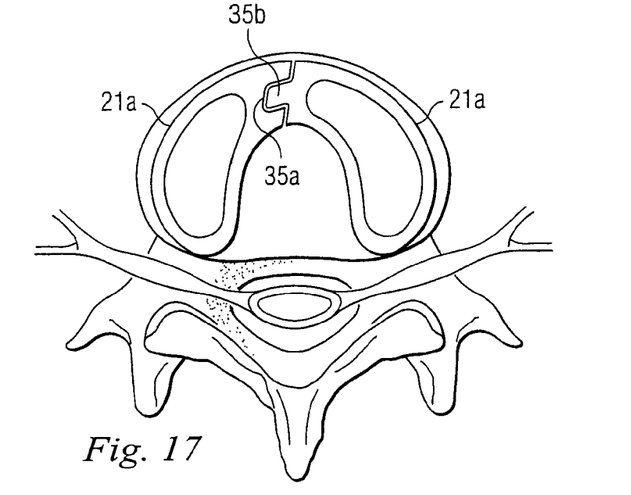
FIG. 17 is a transverse, bottom-up-view of a portion of a lumbar spine showing the superior portion of a fourth embodiment of an artificial intervertebral joint constructed according to the principles of the disclosure in which the facet joints are not replaced.
Figure 18:
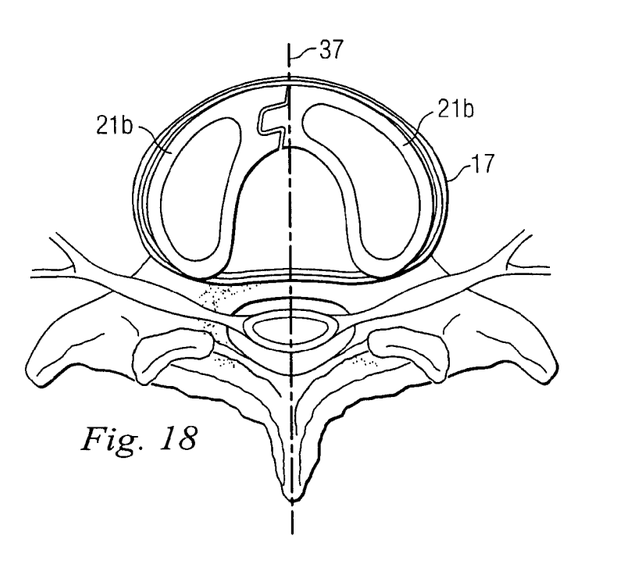
FIG. 18 is a transverse, top-down-view of a portion of a lumbar spine showing the inferior portion of the fourth embodiment of an artificial intervertebral joint.

FIGS. 17 and 18 illustrate a fourth embodiment of an artificial intervertebral joint. In the exemplary embodiment illustrated in FIGS. 17 and 18, the artificial intervertebral joint may have all of the features discussed above except for artificial facet components. In this embodiment, the natural facet joints remain. The ligamentous tension band may also be left intact in some embodiments. In addition, this embodiment includes a specific example of an anterior midline connection between respective upper and lower retaining portions, which assists in maintaining the placement of the first retaining portion 21*a* and the second retaining portion 21*b*.

FIGS. 17 and 18 illustrate that it is possible to provide a first retaining portion 21*a* with a lock and key type pattern which is complemented by the corresponding mating portion provided on the second retaining portion 21*b*. More particularly, one half of the first retaining portion 21*a* has an outer boundary with a U-shaped portion 35*a* while the other half of the corresponding first retaining portion 21*a* has an outer boundary with a protruding portion 35*b*, which fits into the U-shaped portion 35*a*. As a result, each half of the first retaining portion 21*a*, 21*b* may be maintained in a predetermined position. However, the upper or lower retaining portions may fit together and/or be connected in the interbody space, e.g., near their midline anterior portions, in any manner that facilitates implantation and/or assists in providing and/or retaining the joint in a generally stable, symmetrical configuration. It may be even more important to provide such connection between the lower retaining portions due to the inward forces provided by annulus 17 remaining on the inferior end plate as shown in FIG. 18. A midline connection between the respective lower retaining portions will resist the force of the outer annulus tending to cause migration of the retaining portions toward the midline 37.

As shown in the various exemplary embodiments, other than the portions of the first and/or second retaining portions which may fit together like a lock and key to maintain the placement of the portions relative to each other, each half of the artificial intervertebral joint may be generally symmetrical about the midline 37 of the vertebrae.

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the halves of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right halves of the retaining members are fitted together and held in place by the outer annulus. As such, the remaining portion of the annulus may be in substantially the same place as it was prior to the procedure.

Further, in the cases where the annulus of the natural disc must be removed completely or this is insufficient annulus remaining, it is possible, for example, to use the embodiment of the disclosure where the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorally. The anterior and posteriorally placed portions could be fitted together similar to the embodiment shown in FIGS. 17 and 18.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An artificial spinal joint for creating at least a portion of a coupling between a superior vertebra and an inferior vertebra comprising:
   an anterior joint replacement component including
       an upper retaining member having an upper endplate contact surface adapted to contact an endplate of the superior vertebra, and an upper joint surface;
       a lower retaining member having a lower endplate contact surface adapted to contact an endplate of the inferior vertebra and an integrally formed lower joint surface, wherein the upper joint surface is in contact with the lower joint surface and the upper and lower joint surfaces are slidably engaged;
   a bridge having a proximal end and a distal end, the bridge coupled to the anterior joint replacement component at the proximal end; and
   a posterior joint replacement component coupled to the distal end of the bridge and sized to extend posteriorly outside of a disc space defined between the endplates of the superior and inferior vertebrae and including an upper articulation face fit together in articulating engagement with a lower articulation face.

2. The artificial spinal joint of claim 1 wherein the coupling between the anterior joint replacement component and the bridge is a rigid coupling.

3. The artificial spinal joint of claim 1 wherein the coupling between the posterior joint replacement component and the bridge is a rigid coupling.

4. The artificial spinal joint of claim 1 wherein the artificial spinal joint includes a connection for accepting a fastener for fixing the artificial spinal joint to the superior vertebra.

5. The artificial spinal joint of claim 4 wherein the connection for accepting a fastener is integral with the anterior joint replacement component.

6. The artificial spinal joint of claim 4 wherein the connection for accepting a fastener is integral with the posterior joint replacement component.

7. The artificial spinal joint of claim 1 wherein the artificial spinal joint includes a connection for accepting a fastener for fixing the artificial spinal joint to the inferior vertebra.

8. The artificial spinal joint of claim 7 wherein the connection for accepting a fastener is integral with the anterior joint replacement component.

9. The artificial spinal joint of claim 7 wherein the connection for accepting a fastener is integral with the posterior joint replacement component.

10. The artificial spinal joint of claim 1 wherein the bridge is sized to extend posteriorly outside of the disc space.

11. The artificial spinal joint of claim 1 wherein the artificial spinal joint includes at least:
    an upper member comprising
        the upper retaining member,
        an upper portion of the bridge coupled to the upper retaining member, and
        an upper portion of the posterior joint replacement component coupled to the upper portion of the bridge; and
    a lower member comprising
        the lower retaining member,
        a lower portion of the bridge coupled to the lower retaining member, and
        a lower portion of the posterior joint replacement component coupled to the lower portion of the bridge.

12. The artificial spinal joint of claim 11 wherein the upper and lower portions of the posterior joint replacement component are connected with a band.

13. The artificial spinal joint of claim 1 wherein the bridge is at least a portion of an artificial pedicle.

14. An artificial spinal joint comprising:
    a disc replacement component including
        an upper retaining member comprising an upper vertebral endplate contact surface, configured to engage an endplate of an upper generally cylindrical vertebral body portion of an upper vertebra, and an upper joint surface and
        a lower retaining member comprising a lower vertebral endplate contact surface, configured to engage an endplate of a lower generally cylindrical vertebral body portion of a lower vertebra, and a lower joint surface, wherein the upper joint surface is in contact with the lower joint surface and the upper and lower joint surfaces are disposed between the upper and lower vertebral endplate contact surfaces and are slidably engaged;
    an artificial facet component spaced a posterior distance apart from the disc replacement component, the artificial facet component including an upper articulation face fit in mating and articulating engagement with a lower articulation face; and
    a fixation bridging component sized to extend posteriorly outside a disc space between the upper and lower generally cylindrical vertebral body portions and posteriorly beyond the upper and lower generally cylindrical vertebral body portions, the fixation bridging component connected between the disc replacement component and the lower articulation face of the artificial facet component such that the fixation bridging component positions the artificial facet component posteriorly beyond and spaced apart from the upper and lower generally cylindrical vertebral body portions.

15. The artificial spinal joint of claim 14 further comprising: a securing component configured to secure the upper vertebral endplate contact surface to the endplate of the upper generally cylindrical vertebral body portion of the upper vertebra.

16. The artificial spinal joint of claim 15 wherein the securing component extends through a securing support that extends from the artificial facet component.

17. The artificial spinal joint of claim 14 wherein the lower retaining member comprises an integrally formed spacer component which includes the lower joint surface.

18. The artificial spinal joint of claim 14 wherein the disc replacement component comprises separated left and right disc portions, the artificial facet component comprises separated left and right facet portions, and the fixation bridging component comprises a left fixation portion extending between the left disc portion and the left facet portion and a right fixation portion extending between the right disc portion and the right facet portion.

19. The artificial spinal joint of claim 14 wherein the fixation bridging component is also connected between the disc replacement component and the upper articulation face of the artificial facet component.

* * * * *